US008415518B2

(12) United States Patent
Hall et al.

(10) Patent No.: US 8,415,518 B2
(45) Date of Patent: *Apr. 9, 2013

(54) PRODUCTION OF LIGHT OLEFINS

(75) Inventors: Richard B. Hall, Whitehouse Station, NJ (US); Guang Cao, Branchburg, NJ (US); Christopher David William Jenkins, South Caulfield (AU); James R. Lattner, LaPorte, TX (US); Michael J. Veraa, Houston, TX (US); Thomas H. Colle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 741 days.

This patent is subject to a terminal disclaimer.

(21) Appl. No.: 11/818,333

(22) Filed: Jun. 14, 2007

(65) Prior Publication Data

US 2008/0033225 A1 Feb. 7, 2008

Related U.S. Application Data

(60) Provisional application No. 60/835,280, filed on Aug. 3, 2006, provisional application No. 60/849,085, filed on Oct. 3, 2006.

(51) Int. Cl.
*C07C 1/20* (2006.01)
(52) U.S. Cl. ........ 585/640; 585/329; 585/501; 585/638; 585/639
(58) Field of Classification Search .................. 585/520, 585/525, 329, 501, 638, 639, 640, 641; 502/208, 502/214
See application file for complete search history.

(56) References Cited

U.S. PATENT DOCUMENTS

| 4,404,414 A | 9/1983 | Penick et al. |
| 4,544,538 A | 10/1985 | Zones |
| 4,590,320 A | 5/1986 | Sapre |
| 4,665,249 A | 5/1987 | Mao et al. |
| 4,826,662 A | 5/1989 | Mao et al. |
| 5,059,738 A | 10/1991 | Beech, Jr. et al. |
| 5,602,289 A * | 2/1997 | van Dijk ................ 585/315 |

(Continued)

FOREIGN PATENT DOCUMENTS

| WO | WO 03/020641 | 3/2003 |
| WO | WO 03/078324 | 9/2003 |
| WO | WO 2005/063623 | 6/2006 |
| WO | WO 2006/057760 | 6/2006 |

OTHER PUBLICATIONS

De Chen et al., "The effect of crystal size of SAPO-34 on the selectivity and deactivation of the MTO reaction," Microporous and Mesoporous Materials, vol. 29, pp. 191-203, 1999.

(Continued)

*Primary Examiner* — In Suk Bullock
*Assistant Examiner* — Bradley Etherton
(74) *Attorney, Agent, or Firm* — Kevin M. Faulkner; David M. Weisberg

(57) ABSTRACT

This invention is directed to a process for producing olefin product from an oxygenate feed that includes dimethyl ether (DME). The process uses an olefin forming catalyst that contains a porous crystalline material, preferably a porous crystalline aluminosilicate molecular sieve material. The process produces high quantities of light olefin (i.e., ethylene, propylene, and mixtures thereof).

26 Claims, 1 Drawing Sheet

U.S. PATENT DOCUMENTS

| | | | |
|---|---|---|---|
| 6,334,994 B1 | 1/2002 | Wendelbo et al. | |
| 6,812,372 B2 | 11/2004 | Janssen et al. | |
| 6,844,291 B2 | 1/2005 | Levin et al. | |
| 7,045,672 B2 | 5/2006 | Xu et al. | |
| 7,071,136 B2 | 7/2006 | Chang et al. | |
| 7,094,389 B2 | 8/2006 | Cao et al. | |
| 7,148,172 B2 | 12/2006 | Strohmaier et al. | |
| 7,232,936 B1* | 6/2007 | Yurchak | 585/640 |
| 7,435,863 B2* | 10/2008 | Strohmaier et al. | 585/640 |
| 7,622,624 B2 | 11/2009 | Mertens et al. | |
| 2002/0165089 A1* | 11/2002 | Janssen et al. | 502/214 |
| 2003/0176751 A1* | 9/2003 | Strohmaier et al. | 585/639 |

OTHER PUBLICATIONS

De Chen, et al., Dimethyl ether conversion to light olefins over SAPO-34: Deactivation due to coke deposition, Studies in Surface Science and Catalysis, V. 199, pp. 521-526, 1998.

De Chen et al., "The Role of Coke Deposition in the Conversion of Methanol to Olefins over SAPO-34", Elsevier Science B.V., Catalyst Deactivation 1997, pp. 159-166.

Lun-Teh Yuen et al., "Product selectivity in methanol to hydrocarbon conversion for isostructural compositions of AFI and CHA molecular sieves", Microporous Materials, 2 (1994) pp. 105-117.

* cited by examiner

PRODUCTION OF LIGHT OLEFINS

CROSS REFERENCE TO RELATED APPLICATIONS

This claims the benefit of and priority from U.S. Ser. No. 60/835,280, filed Aug. 3, 2006 and 60/849,085, filed Oct. 3, 2006. The above applications are fully incorporated herein by reference.

FIELD OF THE INVENTION

This invention relates to the production of light olefins, such as ethylene and propylene, from oxygenates. In particular, this invention relates to the production of light olefins from an oxygenate feed-containing dimethyl ether and using a catalyst containing a porous crystalline material.

BACKGROUND OF THE INVENTION

Oxygenate to olefins reaction systems typically convert oxygenates to olefin products. In particular, methanol to olefins reaction systems utilize methanol as the primary feed for the conversion process, and these processes typically use molecular sieves as catalysts.

Silicoaluminophosphate (SAPO) molecular sieves have generally been considered to be desirable catalytic materials in converting oxygenate feedstocks to olefin compositions. These catalysts are particularly good catalysts for making olefins such as ethylene and propylene from oxygenate compounds.

Alternative catalysts to the SAPO molecular sieves have also been sought. Particularly desirable alternatives have included those catalysts that have a high selectivity to ethylene and propylene, are highly attrition resistant and are, of course, those that are more efficiently used in the overall oxygenate to olefin production process.

U.S. Pat. No. 7,071,136 discloses molecular sieves containing [$AlO_4$] and [$SiO_4$] tetrahedral units can be used as a catalyst to convert methanol to olefins such as ethylene and propylene. The particular catalysts are considered to be highly attrition resistant, which is a preferred characteristic for the operation of the reaction system.

U.S. Pat. No. 6,844,291 B2 discloses a molecular sieve catalyst composition that includes a metal oxide. Combining the metal oxide with the molecular sieve was considered to enhance olefin yield and catalyst lifetime in the oxygenate to olefin reaction process.

U.S. Patent Publ. No. 2003/0176751 describes a porous crystalline material that has a chabazite framework type and involves the molar relationship: $X_2O_3:(n)YO_2$, where X is a trivalent element, such as aluminum, boron, iron, indium, and/or gallium; Y is a tetravalent element such as silicon, tin, titanium and/or germanium; and n is greater than 100. The material is synthesized in a fluoride medium and exhibits activity and selectivity in the conversion of methanol to lower olefins, especially ethylene and propylene.

U.S. Pat. No. 7,094,389 discloses a crystalline material substantially free of framework phosphorus and comprising a CHA framework type molecular sieve with stacking faults or at least one intergrown phase of a CHA framework type molecular sieve and an AEI framework type molecular sieve. The material in its calcined, anhydrous form, involves the molar relationship: $(n)X_2O_3:YO_2$, where X is a trivalent element; Y is a tetravalent element; and n is from 0 to about 0.5. The material exhibits activity and selectivity in the conversion of methanol to lower olefins, especially ethylene and propylene.

Various catalyst pretreatment methods are also used to increase the amount of light or prime olefins (i.e., ethylene or propylene, or mixtures thereof) produced in the methanol to olefins conversion processes. For example, U.S. Pat. No. 7,045,672 is directed to processes for making olefin product from an oxygenate feed that includes a step of pretreating a fresh or regenerated metalloaluminophosphate molecular sieve, which is low in carbon content, with a dimethyl ether composition. The dimethyl ether in the composition forms a hydrocarbon co-catalyst within the pore structure of the molecular sieve, and the pretreated molecular sieve containing the co-catalyst is used to convert oxygenate to an olefin product, with high selectivity to light olefins.

Although advances have been made in increasing the amount of ethylene and propylene produced in the oxygenate to olefins conversion reaction, further increases in these amounts are sought. In certain cases, it is particularly desirable to increase the amount of ethylene produced relative to the propylene.

SUMMARY OF THE INVENTION

This invention provides a process for producing an olefin product that is high in ethylene and propylene content. The process is particularly beneficial in producing higher quantities of ethylene relative to that of propylene.

According to one aspect of the invention, there is provided a process for producing an olefin product. The process comprises contacting an oxygenate feed containing at least 15 wt % dimethyl ether, preferably at least 25 wt %, more preferably at least 30 wt %, and still more preferably at least 50 wt % dimethyl ether, based on total weight of the feed, with an olefin forming catalyst to form the olefin product. Preferably, the catalyst contains a porous crystalline material, preferably a porous crystalline aluminosilicate molecular sieve material, having a chabazite or AEI framework, or a mixture or intergrowth containing a chabazite and AEI framework with a molar relationship of:

$$X_2O_3:(n)YO_2,$$

wherein X is a trivalent element, Y is a tetravalent element and n is greater than 20, preferably at least 30, more preferably at least 50, and still more preferably at least 100.

According to another aspect of the invention, there is provided a process for producing an olefin product in which an olefin forming catalyst is provided that contains a porous crystalline material having a chabazite or AEI framework, or a mixture or intergrowth containing a chabazite and AEI framework with a molar relationship of:

$$X_2O_3:(n)YO_2:(m)R:zH_2O,$$

wherein X is a trivalent element, Y is a tetravalent element, n is greater than 20, preferably at least 30, more preferably at least 50, and still more preferably at least 100, R is a directing agent, m ranges from 15 to 350, and z ranges from 0 to 10. The directing agent is removed to form an active olefin forming catalyst, and the active olefin forming catalyst is contacted with an oxygenate feed containing at least 15 wt % dimethyl ether, based on total weight of the feed, to form the olefin product.

In one embodiment, R comprises at least one cyclic amine or ammonium compound. Alternatively, R comprises at least one multi-cyclic amine or ammonium compound.

In another embodiment, m ranges from about 30 to about 50. In still another embodiment, n is from about 200 to about 2000, preferably from about 200 to about 1200.

In another embodiment, X is selected from aluminum, boron, iron, indium, and/or gallium and Y is selected from silicon, tin, titanium and/or germanium. Preferably, X is aluminum and Y includes silicon.

In another embodiment, the oxygenate feed is contacted with the olefin forming catalyst at an average reactor temperature in the range of from 200° C. to 1000° C.

In another embodiment, the oxygenate feed is a mixed feed that contains not greater than 40 wt % methanol and at least 40 wt % dimethyl ether, based on total weight of the oxygenate feed. Preferably, the oxygenate feed is a mixed feed that contains not greater than 35 wt % methanol and at least 50 wt % dimethyl ether, based on total weight of the oxygenate feed.

In yet another embodiment, the olefin forming catalyst is contacted with a second oxygenate feed containing at least 50 wt % methanol, based on total weight of the second oxygenate feed.

In an alternative embodiment, the olefin forming catalyst is contacted with the oxygenate feed until the olefin forming catalyst is deposited with a coke deposit of 20% or more, based on percent of maximum coke content, and the coke deposited catalyst is then contacted with a second oxygenate feed containing at least 50 wt % methanol, based on total weight of the second oxygenate feed.

In another embodiment of the invention, olefin from the olefin product is contacted with a polyolefin forming catalyst to form a polyolefin.

DETAILED DESCRIPTION OF THE INVENTION

Figure 1:
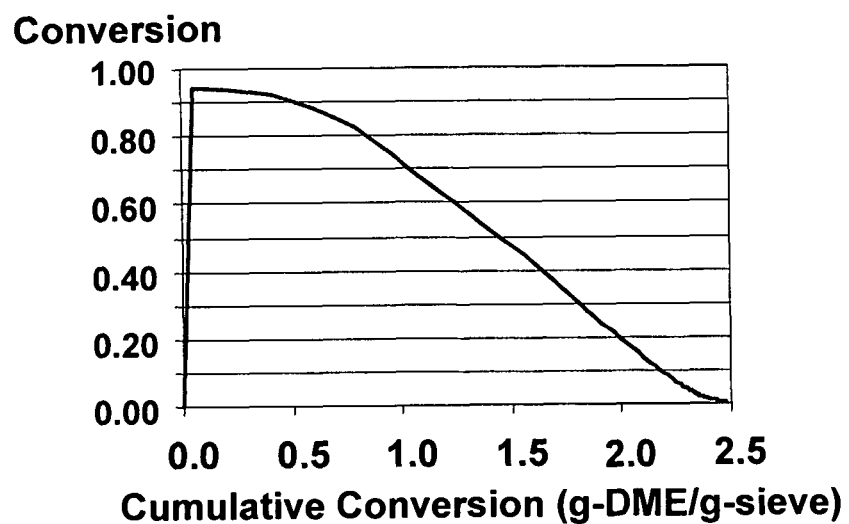
FIG. 1 is a graph showing conversion of dimethyl ether to olefin product over a porous crystalline material having a chabazite framework.
Figure 2:
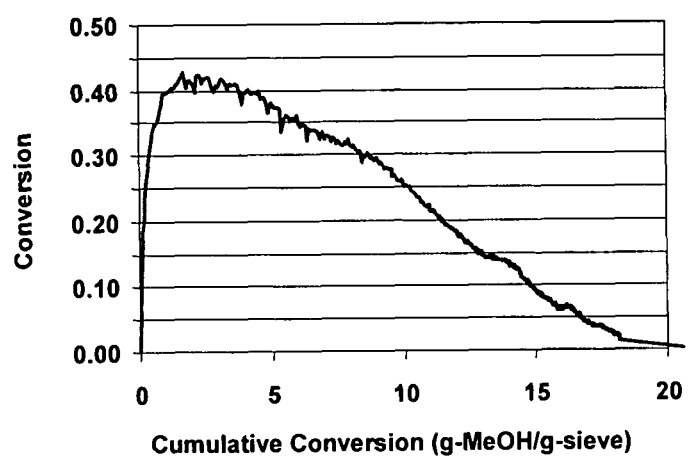
FIG. 2 is a graph showing conversion of methanol to olefin product using a porous crystalline material having a chabazite framework that was previously used to convert dimethyl ether to olefin product.

Production of Olefin Product High in Ethylene Content

This invention is particularly directed to a process for producing olefin product from an oxygenate feed that includes a quantity of dimethyl ether (DME) effective for increasing the production of ethylene relative to that using 100 wt % methanol feed. The increase in ethylene production is realized when the dimethyl ether containing feed contacts an olefin forming catalyst that contains a porous crystalline material, preferably a porous crystalline aluminosilicate molecular sieve material, having a chabazite or AEI framework, or a mixture or intergrowth containing a chabazite and AEI framework. The process produces, overall, high quantities of light olefin (i.e., ethylene, propylene, and mixtures thereof), which can be used in the manufacture of polyolefins such as polyethylene and polypropylene. The process is particularly beneficial in producing olefin product that has high ethylene content relative to propylene content.

DME Feed

In this invention, oxygenate feed is contacted with the olefin forming catalyst to form the olefin product. The oxygenate feed includes dimethyl ether (DME). Preferably, the oxygenate feed contains at least 15 wt % dimethyl ether, more preferably at least 20 wt %, still more preferably at least 25 wt %, more preferably at least 30 wt %, more preferably at least 50 wt %, and still more preferably at least 60 wt % DME, based on total weight of the feed.

The oxygenate feed can also include other oxygenates besides DME. Such oxygenates include one or more organic compound(s) containing at least one oxygen atom. Preferably, the oxygenate includes one or more alcohol(s), preferably aliphatic alcohol(s) where the aliphatic moiety of the alcohol(s) has from 1 to 4 carbon atoms, preferably from 1 to 3 carbon atoms, and most preferably from 1 to 2 carbon atoms.

Non-limiting examples of specific types of oxygenates useful in the invention along with the DME include methanol, ethanol, n-propanol, isopropanol, methyl ethyl ether, diethyl ether, di-isopropyl ether, formaldehyde, dimethyl carbonate, dimethyl ketone, acetic acid, and mixtures thereof. In a preferred embodiment, the feed also includes, in addition to DME, at least one oxygenate selected from the group consisting of methanol, ethanol, and diethyl ether; more preferably methanol.

In addition to DME, and optionally one or more other oxygenate component, the feed can include one or more diluent(s), which are generally non-reactive to the feed or catalyst composition and are typically used to reduce the concentration of the feed. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feed entering a reactor or added directly to the reactor, or added with the catalyst composition.

In a preferred embodiment of the invention, the catalyst is contacted with dimethyl ether and methanol-containing feed or feeds. The feed can be a co-feed (i.e., mixtures such as a mixture of DME and methanol) or the feed can be staged (i.e., alternated type contacting of feed and catalyst such as alternating contacting catalyst with DME and methanol).

In one embodiment, the oxygenate feed contains at least 50 wt % methanol, based on total weight of the oxygenate feed. Preferably, the oxygenate feed contains at least 60 wt % methanol, more preferably at least 70 wt % methanol, based on total weight of the oxygenate feed. In a preferred embodiment in which the oxygenate feed contains at least 50 wt % methanol, based on total weight of the oxygenate feed, the feed is a second feed, with the catalyst having previously contacted with a first feed containing dimethyl ether. Preferably, the first feed contains a major amount of the dimethyl ether.

In one embodiment, the oxygenate feed is a mixed feed that contains dimethyl ether and methanol. In a particular embodiment, the mixed feed is comprised of not greater than 40 wt % methanol, based on total weight of the oxygenate feed. Preferably, the mixed feed is comprised of not greater than 35 wt % methanol, more preferably not greater than 30 wt % methanol, based on total weight of the oxygenate feed. Preferably, the mixed feed contains at least 40 wt % dimethyl ether, more preferably at least 50 wt % dimethyl ether, even more preferably at least 60 wt % dimethyl ether, and most preferably at least 70 wt % dimethyl ether.

In another embodiment, the olefin forming catalyst is contacted with a first oxygenate feed containing a major amount of dimethyl ether and a second oxygenate feed containing a minor amount of dimethyl ether. Major means at least 50 wt %, based on total weight of the feed. Minor means less than 50 wt %, based on total weight of the feed. The contact is preferably in staged mode, as previously described.

In one type of staged process, the olefin forming catalyst is contacted with the oxygenate feed until the dimethyl ether conversion is less than 50%. Preferably, the olefin forming catalyst is contacted with the oxygenate feed until the dimethyl ether conversion is less than 60%, more preferably less than 70%. The olefin forming catalyst is then contacted with a second oxygenate feed containing alcohol, preferably methanol. The second oxygenate feed preferably contains the amount of alcohol, particularly methanol, already noted.

In another type of staged process, contact of feed with the olefin forming catalyst is controlled by the degree of coke deposited on the catalyst during the conversion process. Preferably, the olefin forming catalyst is contacted with the oxygenate feed until the olefin forming catalyst is deposited with a coke deposit of 20% or more, based on percent of maximum coke content. The maximum coke content is the maximum amount of coke that can be deposited on the catalyst during the reaction process. Preferably, the olefin forming catalyst is deposited with a coke deposit of 30% or more, more preferably at least 40% or more. Then, the coke deposited catalyst is contacted with a second oxygenate feed containing alcohol, preferably methanol.

Product Produced

The feed is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

According to the invention, a substantial quantity of light olefins is produced, with light olefins being defined as ethylene and propylene. In one embodiment, the amount of light olefins produced, based on the total weight of hydrocarbon produced, is greater than 50 weight percent. Preferably, the amount of light olefins produced is greater than 65 weight percent, more preferably greater than 75 weight percent, based on total weight of hydrocarbon produced. Typically, the amount ethylene produced in weight percent based on the total weight of hydrocarbon product produced, is greater than 30 weight percent, preferably greater than 35 weight percent, and more preferably greater than 40 weight percent. In addition, the amount of propylene produced in weight percent based on the total weight of hydrocarbon product produced is greater than 20 weight percent, preferably greater than 25 weight percent, and more preferably greater than 30 weight percent.

The olefin product that is produced is particularly high in ethylene content when using the desired feed and catalyst combination. Preferably, the ethylene content of the product that is produced will be greater than that of propylene.

In one embodiment, the contacting of the oxygenate with the olefin forming catalyst forms an olefin product having an ethylene to propylene weight ratio increased by at least 5% relative to that when using 100 wt % methanol as feed at the same conversion conditions. Preferably, the olefin product has an ethylene to propylene weight ratio that is increased by at least 8%, more preferably at least 10%, relative to that when using 100 wt % methanol as feed at the same conversion conditions.

In one embodiment, the oxygenate contacts an olefin forming aluminosilicate catalyst, which includes at least in part a CHA type framework, at an average reactor temperature of from 520° C. to 1000° C. and forms an olefin product having an ethylene to propylene weight ratio of at least 1.35, based on total weight of the olefin product produced as a cycle weighted average. Cycle weighted average is determined by measuring the product formed over a fresh, uncoked catalyst, until the catalyst becomes deactivated. A catalyst is considered to be deactivated when feed conversion over the catalyst drops below 10%. Preferably, at an average reactor temperature of from 520° C. to 1000° C., the contacting of the oxygenate with the olefin forming catalyst forms an olefin product having an ethylene to propylene weight ratio of at least 1.4, more preferably at least 1.5, based on total weight of the olefin product produced as a cycle weighted average.

In another embodiment, the oxygenate contacts an olefin forming aluminosilicate catalyst, which includes at least in part a CHA type framework, at an average reactor temperature of from 200° C. to less than 520° C. and forms an olefin product having an ethylene to propylene weight ratio of at least 1.0, based on total weight of the olefin product produced as a cycle weighted average. Preferably, at an average reactor temperature of from 200° C. to less than 520° C., the contacting of the oxygenate with the olefin forming catalyst forms an olefin product having an ethylene to propylene weight ratio of at least 1.1, more preferably at least 1.2, based on total weight of the olefin product produced as a cycle weighted average.

At least a portion of the DME that is used in the feed can be made from methanol. Since DME is relatively volatile compared to methanol, it is generally transported either as a refrigerated or pressurized liquid. This requires specialized tanks and ships, and as a result it costs around twice as much to ship DME (on an energy basis) as it does to ship methanol. Hence, for the case where an oxygenate feed such as methanol is produced at a separate location from where the oxygenate to olefin conversion plant is located, the high transportation cost of DME can have some degree of offset to the economic benefit for feeding DME as a feedstock for conversion into olefin.

In one embodiment of the invention, methanol is transported to a location geographically distinct from that where the methanol composition was manufactured or where it was separated from the originally produced crude methanol stream. Preferably, this methanol is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to a conversion unit to convert the methanol to dimethyl ether. The dimethyl ether is then used as a feedstock in an oxygenate to olefin reaction system.

The methanol that is either converted to DME or that is used in the oxygenate to olefin reaction system is preferably loaded onto a ship and then transported to the DME conversion facility or oxygenate to olefin reaction facility. Preferably, the ship is able to contain at least 20,000 tons, preferably at least 40,000 tons, and more preferably at least 80,000 tons.

Another advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

Methanol can be converted to DME using any appropriate process. In general, the methanol is heated to a temperature of from 200° C. to 400° C. and fed to a reactor containing an acid catalyst. The methanol is converted by exothermic dehydration to DME and water. Conversion of methanol to DME is equilibrium limited to about 70 wt % to about 85 wt % depending on the specific catalyst and process conditions. Hence, the reactor effluent comprises a mixture of DME, water and unconverted methanol.

The methanol that is sent to the DME reactor as a feed stream typically contains some water. In one embodiment, the methanol feed stream that is sent to the DME reactor contains from 0.1 wt % to 20 wt % water. Preferably, the methanol feed stream that is sent to the DME reactor contains from 1 wt % to 10 wt % water, more preferably from 2 wt % to 8 wt % water, based on the total weight of the feed stream to the DME reactor.

Some or all of the water in the DME product can be removed from the product or the DME product can be sent to the oxygenate to olefins reaction system as is, including water. In one embodiment, DME reaction product is recovered from the DME reactor and cooled at a temperature in which water and unconverted methanol in the DME product is condensed. At least a majority of the DME in the DME product is then recovered in vapor form, and ultimately sent to the oxygenate to olefin reaction system.

Condensed water and unreacted methanol recovered from the DME reaction product can be sent to a separation unit if desired. Preferably, a methanol rich stream is recovered from the separation unit as an overhead stream and a water rich stream is recovered from the separation unit as a bottoms stream.

Process Conditions

The process can be conducted over a wide range of reactor temperatures. For example, average reactor temperatures are in the range of from about 200° C. to about 1000° C. Preferably, the average reactor temperatures are in the range of from about 250° C. to about 800° C.; more preferably from about 250° C. to about 750° C., or from about 300° C. to about 650° C., or from about 350° C. to about 600° C., and most preferably from about 400° C. to about 600° C.

Similarly, the process can be conducted over a wide range of pressures including autogenous pressure. Typically the partial pressure of the oxygenate exclusive of any diluent therein employed in the process is in the range of from about 0.1 kPaa to about 5 MPaa, such as from about 5 kPaa to about 1 MPaa, and preferably from about 20 kpaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^-$, and conveniently from about 10 $hr^{-1}$ to about 1000 $hr^{-1}$. In one embodiment, the WHSV is greater than 5 $hr^{-1}$ and, where feedstock contains methanol and/or dimethyl ether, is in the range of from about 5 $hr^{-1}$ to about 300 $hr^{-1}$.

In one embodiment, the process is conducted in a fluidized bed. Preferably, the superficial gas velocity (SGV) of the total feedstock, including diluent and reaction products within the reactor system, and particularly within a riser reactor(s), is at least 0.1 meter per second (m/sec), more preferably greater than 0.5 m/sec.

In another embodiment, the process is conducted in a fast fluidized bed mode, such as in a riser reactor. Preferably, the process is carried out in a reactor at a SGV of greater than 1 m/sec, more preferably greater than 2 m/sec, even more preferably greater than 3 m/sec, and still more preferably greater than 4 m/sec.

In one embodiment, the process is conducted as a fixed bed process. In a preferred embodiment, the process is carried out as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796 and 6,287,522 (dual riser), and *Fluidization Engineering*, D. Kunii and O. Levenspiel, Robert E. Krieger Publishing Company, New York, N.Y. 1977.

Preferred reactor types are riser reactors generally described in *Riser Reactor, Fluidization and Fluid-Particle Systems*, pp. 48 to 59, F. A. Zenz and D. F. Othmo, Reinhold Publishing Corporation, New York, 1960, and U.S. Pat. No. 6,166,282 (fast-fluidized bed reactor).

In one embodiment, the process is conducted as a fluidized bed process or high velocity fluidized bed process utilizing a reactor system, a regeneration system and a recovery system. In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

The feedstock entering the reactor system is preferably converted, partially or fully, in one or more reactors into a gaseous effluent that enters a disengaging vessel along with a coked catalyst composition. In one embodiment, cyclone(s) are provided within the disengaging vessel to separate the coked catalyst composition from the gaseous effluent containing olefin product. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

After separation of the gaseous effluent from the coked catalyst, the gaseous effluent is sent to a recovery section of the system where the olefins are separated into components parts. For example, ethylene and propylene, as well as any other olefin product, can be separated and recovered as separate products. The coked catalyst, which contains a carbonaceous layer that was formed during the conversion process, is recovered from the disengaging vessel and can be re-used as is or sent to a regenerator. In the regenerator, the coke or carbonaceous layer is removed by contacting the catalyst, which is still hot from the reaction process, with a regeneration gas to remove some or all of the coke deposit.

Catalyst

The catalyst used in this invention is an olefin forming catalyst that contains a porous crystalline material, preferably a porous crystalline aluminosilicate molecular sieve material, having a chabazite or AEI framework, or a mixture or intergrowth containing a chabazite and AEI framework. In this invention, the crystalline material also has a molar relationship of:

$$X_2O_3:(n)YO_2,$$

wherein X is a trivalent element, Y is a tetravalent element and n is greater than 20, preferably at least 30, more preferably at least 50, and still more preferably at least 100. Alternatively, n is from about 200 to about 2000, preferably from about 200 to about 1200.

In one embodiment of the invention, the crystalline material involves the molar relationship:

$$X_2O_3:(n)YO_2,$$

wherein X is a trivalent element, non-limiting examples of which include aluminum, boron, iron, indium, and/or gallium, preferably aluminum; Y is a tetravalent element, non-limiting examples of which include silicon, tin, titanium and/or germanium, preferably silicon; and n is as previously defined.

In its as-synthesized form, the crystalline material has the molar relationship:

$$X_2O_3:(n)YO_2:(m)R:zH_2O,$$

wherein X, Y and n are as previously defined and wherein m ranges from about 15 to about 350, preferably from about 20 to about 200, more preferably from about 30 to about 50, and z ranges from about 0 to about 10.

The crystalline catalyst material that is used in the invention can be prepared from a reaction mixture containing sources of water, an oxide of a trivalent element X, an oxide of a tetravalent element Y, at least one organic directing agent (R) as described below, and fluoride ions, the reaction mixture having a composition, in terms of mole ratios of oxides, within the following ranges:

| Reactants | Useful | Typical |
|---|---|---|
| $H_2O/YO_2$ | 2-40 | 2-5 |
| $F/YO_2$ | 0-1.0 | 0.3-0.7 |
| $R/YO_2$ | 0.2-2.0 | 0.3-1.0 |
| $X_2O_3/YO_2$ | 0.00025-0.1 | 0.0005-0.01 |

In one embodiment, the organic directing agent R includes at least one compound selected from the group consisting of N-alkyl-3-quinuclidinol, N,N,N-tri-alkyl-1-adamantammonium cations, N,N,N-trialkyl-exoaminonorbornane. Preferably, the organic directing agent R includes a N,N,N-trimethyl-1-adamantammonium cation.

In another embodiment, the organic directing agent R includes at least one compound selected from the group consisting of N,N,N-trimethyl-1-adamantammonium compounds, N,N,N-trimethyl-2-adamantammonium compounds, N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in (1) "Zeolites and Related Microporous Materials: State of the Art 1994," *Studies of Surface Science and Catalysis*, Vol. 84, pp. 29-36; (2) *Novel Materials in Heterogeneous Catalysis* (ed. Terry K. Baker & Larry L. Murrell), Chapter 2, pp. 14-24, May 1990; (3) *J. Am. Chem. Soc.*, 2000, 122, pp. 263-273; and (4) U.S. Pat. Nos. 4,544,538 and 6,709,644. Suitable compounds include hydroxides and salts, such as halides, especially chlorides and fluorides.

In yet another embodiment, the organic directing agent R includes at least one compound selected from the group consisting of N,N-diethyl-2,6-dimethylpiperidinium compounds (mixture or either of the cis/trans isomers), N,N-dimethyl-2,6-dimethylpiperidinium compounds (mixture or either of the cis/trans isomers), and the directing agents cited in *J. Am. Chem. Soc.*, 2000, 122, pp. 263-273 and U.S. Pat. No. 5,958,370. Suitable compounds include hydroxides and salts, such as halides, especially chlorides and fluorides.

In one embodiment, the organic directing agent R comprises at least one cyclic amine or ammonium compound. Preferably, the organic directing agent R comprises at least one multi-cyclic amine or ammonium compound. More preferably, the monocyclic amine or ammonium compound is a substituted piperidine or piperidinium compound, for example a tetraalkylpiperidinium compound, preferably a N,N-diethyl-2,6-dimethylpiperidinium compound. In one embodiment, the multi-cyclic amine or ammonium compound is a tetracyclic amine or ammonium compound, preferably an adamantylamine or ammonium compound, more preferably an N,N,N-trialkyl-1-adamantylammonium compound; most preferably an N,N,N-trimethyl-1-adamantylammonium compound. Suitable ammonium compounds include hydroxides and salts, such as halides, especially chlorides.

In another embodiment, the organic directing agent R comprises a mixture of cyclic amines or ammonium compounds. In one embodiment the a mixture includes a multi-cyclic amine or ammonium compound. Preferably, the mixture includes a multi-cyclic amine or ammonium compound, and a monocyclic amine or ammonium compound. More preferably, the monocyclic amine or ammonium compound comprises a substituted piperidine or piperidinium compound, preferably a tetraalkylpiperidinium compound, more preferably an N,N-diethyl-2,6-dimethylpiperidinium compound. In one embodiment, the multi-cyclic amine or ammonium compound comprises a tetracyclic amine or ammonium compound, preferably an adamantylamine or ammonium compound, more preferably an N,N,N-trialkyl-1-adamantylammonium compound; most preferably an N,N,N-trimethyl-1-adamantylammonium compound. The term multi-cyclic amine is used herein to include multi-cyclic compounds in which the N atom is external to the rings. Suitable ammonium compounds include hydroxides and salts, such as halides, especially chlorides.

Crystallization of the porous crystalline material can be carried out at either static or stirred conditions in a suitable reactor vessel, such as for example, polypropylene jars or Teflon-lined or stainless steel autoclaves, at a temperature of from about 100° C. to about 225° C. for a time sufficient for crystallization to occur at the temperature used, e.g., from about 16 hours to about 7 days. Synthesis of new crystals can be facilitated by the presence of at least 0.01 percent, such as at least 0.10 percent, for example at least 1 percent, seed crystals (based on total weight) of the crystalline product.

After crystallization is complete, the crystals are separated from the mother liquor, washed and calcined to remove the organic directing agent R. Calcination is typically conducted at a temperature of from about 370° C. to about 925° C. for at least 1 minute and generally not longer than 20 hours. If needed, additional activation of the sieve can be effected, such as by cation exchange or acidification.

The crystalline material or molecular sieve used in this invention can include at least in part a chabazite type and an AEI framework or at least one intergrown phase of a CHA framework type and an AEI framework type. Intergrown molecular sieve phases are disordered planar intergrowths of molecular sieve frameworks. Reference is directed to the *Catalog of Disordered Zeolite Structures*, 2000 Edition, published by the Structure Commission of the International Zeolite Association and to the *Collection of Simulated XRD Powder Patterns for Zeolites*, M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

In the case of regular AEI and CHA framework type molecular sieves, the Periodic Building Unit is a double six ring layer. There are two types of layers "a" and "b," which are topologically identical except "b" is the mirror image of "a." When layers of the same type stack on top of one another, i.e. aaaaaaaa or bbbbbbbb, the framework type CHA is generated. When layers "a" and "b" alternate, i.e., abababab, the framework type AEI is generated. Intergrown AEI/CHA molecular sieves comprise regions of CHA framework type sequences and regions of AEI framework type sequences. Each change from a CHA to an AEI framework type sequence results in a stacking fault. In addition, stacking faults can occur in a pure CHA phase material when a sequence of one mirror image layers intersects a sequence of the opposite mirror image layers, such as for example in aaaaaaaabbbbbbbb.

Analysis of intergrown molecular sieves, such as AEI/CHA intergrowths, can be effected by X-ray diffraction and in particular by comparing the observed patterns with calculated patterns generated using algorithms to simulate the effects of stacking disorder. DIFFaX is a computer program based on a mathematical model for calculating intensities from crystals containing planar faults (see M. M. J. Tracey et al., *Proceedings of the Royal Chemical Society*, London, A [1991], Vol. 433, pp. 499-520). DIFFaX is the simulation program selected by and available from the International Zeolite Association to simulate the XRD powder patterns for randomly intergrown phases of zeolites (see *Collection of Simulated XRD Powder Patterns for Zeolites* by M. M. J. Treacy and J. B. Higgins, 2001, Fourth Edition, published on behalf of the Structure Commission of the Int'l. Zeolite Assoc.). It has also been used to theoretically study intergrown phases of AEI, CHA and KFI, as reported by K. P. Lillerud et al. in *Studies in Surface Science and Catalysis*, 1994, Vol. 84, pp. 543-550.

Where the crystalline material of the invention comprises a mixture of CHA and AEI or an intergrowth of a CHA framework type molecular sieve and an AEI framework type molecular sieve, the material can possess a widely varying AEI/CHA ratio of from about 99:1 to about 1:99, such as from about 98:2 to about 2:98, for example from about 95:5 to 5:95. In one embodiment, where the material is to be used a catalyst in the conversion of oxygenates to olefins, the intergrowth is preferably CHA-rich and has AEI/CHA ratio ranging from about 5:95 to about 30:70. In addition, in some cases the intergrown material of the invention may comprise a plurality of intergrown phases each having a different AEI/CHA ratio. The relative amounts of AEI and CHA framework-type materials in the intergrowth of the invention can be determined by a variety of known techniques including transmission electron microscopy (TEM) and DIFFaX analysis, using the powder X-ray diffraction pattern of a calcined sample of the molecular sieve.

The crystalline material can be incorporated or mixed with other additive materials. Such an admixture is typically referred to as formulated catalyst. Preferably, the additive materials are substantially inert to the conversion dimethyl ether to methanol or other alcohol. That is, the additive materials have little to no effect on the reversion of the dimethyl ether in the feed back to methanol or other alcohol.

In one embodiment, another material resistant to the temperatures and other conditions employed in organic conversion processes is mixed with the crystalline material. Such materials can include catalytically active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a catalytically active material tends to change the conversion and/or selectivity of the catalyst in the oxygenate conversion process. Inactive materials suitably serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials, i.e., clays, oxides, etc., function as binders for the catalyst. It is desirable to provide a catalyst having good crush strength because in commercial use it is desirable to prevent the catalyst from breaking down into powder-like materials.

Naturally occurring clays that can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Other useful binders include inorganic oxides, such as silica, zirconia, titania, magnesia, beryllia, alumina, and mixtures thereof.

In addition to the foregoing materials, the crystalline material used in this invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of crystalline material and inorganic oxide matrix may vary widely. For example, a mixture can include a zeolite content ranging from about 1 to about 90 percent by weight and more usually, particularly when the composite is prepared in the form of beads, in the range of about 2 to about 80 weight percent of the composite.

Olefin Product Recovery and Use

In one embodiment, olefin product and other gases are withdrawn from the reactor and are passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes.

The ethylene and propylene streams produced and recovered according to this invention can be polymerized to form plastic compositions, e.g., polyolefins, particularly polyethylene and polypropylene. Any process capable of forming polyethylene or polypropylene can be used. Catalytic processes are preferred. Particularly preferred are metallocene, Ziegler/Natta, aluminum oxide and acid catalytic systems. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4$+ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4$+ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

EXAMPLES

Example 1

Case I and II

As a base case exemplifying current art, product yields obtained from separate laboratory tests of methanol and DME conversion over a SAPO catalyst were compared. The catalyst was a SAPO-CHA/AEI intergrowth (i.e., a silicoaluminophosphate molecular sieve catalyst having an intergrowth framework of CHA and AEI) with a Si/$Al_2$ ratio=0.12. This represents an acid density of approximately 1 Bronsted acid site per 3 cages. A catalyst charge of 0.010 g was placed in the center of a ¼ inch diameter, 12 inch long, quartz tube reactor. A mixture of methanol and argon or DME and argon was fed to the reactor. Total reactor pressure was 2.0 bar, the partial pressure of methanol (or DME) was approximately 0.5 bar. The flow rate was set such that the superficial contact time of the gases with the catalyst was 0.003 seconds for both runs. The reactor temperature was 450° C. Product and reactant gases were measured as a function of time on stream using both a gas chromatograph (GC) and a calibrated mass spectrometer system. Each run was continued until the catalyst was deactivated to 10% of its initial, fresh, activity. Product yields are expressed as a conversion weighted average over the entire cycle from fresh to deactivated, as shown in Table 1.

TABLE 1

| | | | | Product Yields (wt %) | | | | | |
|---|---|---|---|---|---|---|---|---|---|
| Case | Catalyst | Feed | Peak Conversion | $C_2$= | $C_3$= | $C_4$= | $CH_4$ | POS | POR |
| I | SAPO | MeOH | 80% | 39.6 | 38.6 | 12.8 | 2.6 | 78.2 | 1.03 |
| II | SAPO | DME | 70% | 35.3 | 40.8 | 15.6 | 1.5 | 76.1 | 0.86 |

POS = Prime Olefin Selectivity
POR = Prime Olefin Ratio (ethylene:propylene)

Example 2

Cases III and IV

Runs similar to Example 1 were carried out on an aluminosilicate catalyst having an intergrowth framework of CHA and AEI (referred to as a Si-CHA/AEI intergrowth catalyst) with a Si/Al ratio=200. This represents an acid density of approximately 1 Bronsted acid site per 16 cages. A catalyst charge of 0.010 g was placed in the center of a ¼ inch diameter, 12 inch long, quartz tube reactor. A mixture of methanol and argon or DME and argon was fed to the reactor. Total reactor pressure was 2.0 bar, the partial pressure of methanol (or DME) was approximately 0.5 bar. The flow rate was set such that the superficial contact time of the gases with the catalyst was 0.003 seconds for the DME run and 0.0015 seconds for the methanol run. (The contact times were chosen on the basis of carbon atoms or $CH_2$ groups fed to the reactor such that the contact times should be considered as equivalent.) The reactor temperature was 520° C. Product and reactant gases were measured as a function of time on stream using both a gas chromatograph (GC) and a calibrated mass spectrometer system. Each run was continued until the catalyst was deactivated to 10% of its initial, fresh, activity. Product yields are expressed as a conversion weighted average over the entire cycle from fresh to deactivated, as shown in Table 2.

TABLE 2

| | | | | Product Yields (wt %) | | | | | |
|---|---|---|---|---|---|---|---|---|---|
| Case | Catalyst | Feed | Peak Conversion | $C_2$= | $C_3$= | $C_4$= | $CH_4$ | POS | POR |
| III | Si-CHA/AEI | MeOH | 70% | 47.7 | 33.5 | 12.1 | 0.7 | 81.2 | 1.33 |
| IV | Si-CHA/AEI | DME | 80% | 60.0 | 25.9 | 8.8 | 1.0 | 85.9 | 2.31 |

POS = Prime Olefin Selectivity
POR = Prime Olefin Ratio (ethylene:propylene)

It can be seen the with methanol feed the Si-CHA/AEI catalyst provides 3 wt % improvement in prime olefin selectivity (POS) relative to the SAPO catalyst. It can be further seen, however, that an even greater increase is obtained when DME is fed over the Si-CHA/AEI. There is also a more dramatic increase in the relative yield of ethylene, as indicated by the Prime Olefin (POR) values shown in Table 2.

Similar results are likely for Si/Al ratios greater than 20, particularly for higher ratios of at least 30, more preferably at least 50, and still more preferably at least 100. This is in contrast to the results in Table 1 for SAPO catalyst, where, with DME feed both the POR and POS are lower than they are with methanol feed.

Example 3

Cases V and VI

Catalyst of the type used in Example 2 was used in a staged feed combination run in which DME was fed initially, followed by methanol feed (cases V(a) and V(b), respectively) and also in a run with MeOH feed only (case VI). The conditions for the test runs were similar to those used in Example 2, except that the temperature was slightly higher at 540° C. and the contact time was increased (flow rate decreased) to increase conversion. Total reactor pressure was 2.0 bar, the partial pressure of methanol (or DME) was approximately 0.5 bar.

Case V(a) is considered to be the first portion of a staged feed run in which DME feed was used, and Case V(b) is the second portion of a staged feed run in which methanol was used as feed. At the end of the first stage of the run, the feed is immediately switched from DME to methanol. For comparative purposes, case VI was performed with a methanol-only feed, which was run under the same conditions as in the staged feed run shown in Case V(a)/V(b).

Yields are shown in Table 3.

TABLE 3

| | | | Wt % of | Product Yields (wt %) | | | | | |
|---|---|---|---|---|---|---|---|---|---|
| Case | Catalyst | Feed | total feed | $C_2$= | $C_3$= | $C_4$= | $CH_4$ | POS | POR |
| V(a) | Si-CHA/AEI | DME | 19% | 56.5 | 27.5 | 10.2 | 1.1 | 84 | 2.05 |
| V(b) | Si-CHA/AEI | MeOH | 81% | 45.6 | 34.9 | 12.1 | 1.3 | 80.5 | 1.31 |
| | | (weighted average) | | 47.96 | 33.48 | 11.74 | 1.26 | 81.4 | 1.43 |
| VI | Si-CHA/AEI | MeOH (single feed) | 100% | 45.3 | 33.7 | 113.4 | 1.2 | 79 | 1.34 |

POS = Prime Olefin Selectivity;
POR = Prime Olefin Ratio (ethylene:propylene)

It can be seen in Table 3 that the sum of the yields from the DME plus the methanol run are improved relative to the methanol only run, case VI. Specifically, POS is increased from 79 to 81.4% and POR increases from 1.34 to 1.43, which are considered significant increases.

The staged feed example of Example 3 had, on a dry basis, 19 wt % DME and 81 wt % methanol, based on total amount of feed to the catalyst in both stages of the run, Case V(a) and Case V(b). Because the amount of DME conversion, which is desirable for its higher POS and POR, was limited by catalyst deactivation by coke, higher POS and POR could be reached by feeding lower amounts of methanol, tending toward the high values of POS=85+ and POR=2.0+ for pure DME. The staged feed process of this invention provides operational flexibility in changing product slate, which would be desirable for meeting changing market demand. It is estimated that useful benefits in yields are achieved between 20% DME/80% MeOH and 90% DME/10% MeOH.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention is further illustrated but not limited by the following embodiments.

This invention further relates to:

Embodiment 1

A process for producing an olefin product, comprising:
contacting an oxygenate feed containing at least 15 wt % dimethyl ether, based on total weight of the feed, with an olefin forming catalyst containing a porous crystalline material having a chabazite or AEI framework, or a mixture or intergrowth containing a chabazite and AEI framework with a molar relationship of:

$$X_2O_3:(n)YO_2,$$

wherein X is a trivalent element, Y is a tetravalent element and n is greater than 20; and
forming the olefin product.

Embodiment 2

A process for producing an olefin product, comprising:
providing an olefin forming catalyst containing a porous crystalline material having a chabazite or AEI framework, or a mixture or intergrowth containing a chabazite and AEI framework with a molar relationship of:

$$X_2O_3:(n)YO_2:(m)R:zH_2O,$$

wherein X is a trivalent element, Y is a tetravalent element, n is greater than 20, R is a directing agent, m ranges from 15 to 350, and z ranges from 0 to 10;
removing the directing agent to form an active olefin forming catalyst; and
contacting the active olefin forming catalyst with an oxygenate feed containing at least 15 wt % dimethyl ether, based on total weight of the feed, to form the olefin product.

Embodiment 3

The process of embodiment 2, wherein R comprises at least one cyclic amine or ammonium compound.

Embodiment 4

The process of embodiment 2, wherein R comprises at least one multi-cyclic amine or ammonium compound.

Embodiment 5

The process of any of the preceding embodiments, wherein m ranges from about 30 to about 50.

Embodiment 6

The process of any of the preceding embodiments, wherein n is at least 30.

Embodiment 7

The process of any of the preceding embodiments, wherein n is at least 50.

Embodiment 8

The process of any of the preceding embodiments, wherein n is at least 100.

Embodiment 9

The process of any of the preceding embodiments, wherein X is selected from aluminum, boron, iron, indium, and/or gallium and Y is selected from silicon, tin, titanium and/or germanium.

Embodiment 10

The process of any of the preceding embodiments, wherein X is aluminum and Y includes silicon.

Embodiment 11

The process of any of the preceding embodiments, wherein oxygenate feed contains at least 25 wt % dimethyl ether, based on total weight of the feed.

Embodiment 12

The process of any of the preceding embodiments, wherein oxygenate feed contains at least 30 wt % dimethyl ether, based on total weight of the feed.

Embodiment 13

The process of any of the preceding embodiments, wherein oxygenate feed contains at least 50 wt % dimethyl ether, based on total weight of the feed.

Embodiment 14

The process of any of the preceding embodiments, wherein the oxygenate feed is contacted with the olefin forming catalyst at an average reactor temperature in the range of from 200° C. to 1000° C.

Embodiment 15

The process of any of the preceding embodiments, wherein the oxygenate feed is a mixed feed that contains not greater than 40 wt % methanol and at least 40 wt % dimethyl ether, based on total weight of the oxygenate feed.

Embodiment 16

The process of any of the preceding embodiments, wherein the oxygenate feed is a mixed feed that contains not greater than 35 wt % methanol and at least 50 wt % dimethyl ether, based on total weight of the oxygenate feed.

Embodiment 17

The process of any of the preceding embodiments, wherein the olefin forming catalyst is contacted with a second oxygenate feed containing at least 50 wt % methanol, based on total weight of the second oxygenate feed.

Embodiment 18

The process of any of the preceding embodiments, wherein the contacting of the oxygenate with the olefin forming catalyst forms an olefin product having an ethylene to propylene weight ratio increased by at least 5% relative to that when using 100 wt % methanol as feed at the same conversion conditions.

Embodiment 19

The process of any of the preceding embodiments, wherein the olefin forming catalyst is contacted with the oxygenate feed until the olefin forming catalyst is deposited with a coke deposit of 20% or more, based on percent of maximum coke content, and the coke deposited catalyst is then contacted with a second oxygenate feed containing at least 50 wt % methanol, based on total weight of the second oxygenate feed.

Embodiment 20

The process of any of the preceding embodiments, wherein olefin from the olefin product is contacted with a polyolefin forming catalyst to form a polyolefin.

Embodiment 21

The process of any of the preceding embodiments, wherein at least one of the following is satisfied: (i) the olefin forming catalyst comprises at least in part a CHA type framework; (ii) the olefin product has an ethylene to propylene weight ratio of at least 1.0, when subject to an average reactor temperature from 200° C. to less than 520° C.; and (iii) the olefin product has an ethylene to propylene weight ratio of at least 1.35, when subject to an average reactor temperature from 520° C. to 1000° C.

What is claimed is:

1. A multi-staged process of alternating contacting an olefin forming catalyst with dimethyl ether (DME) and methanol for producing an olefin product, comprising:
    contacting in a first stage a first oxygenate feed consisting of less than 50 wt % DME, based on the total weight of the feed, as well as diluent, with the catalyst comprising a porous crystalline aluminosilicate;
    contacting in a second stage a second oxygenate feed consisting of at least 50 wt % methanol (MeOH), based on total weight of the feed, as well as diluent, with an olefin forming catalyst comprising a porous crystalline aluminosilicate;
    and recovering an olefin product;
    wherein the porous crystalline aluminosilicate is a mixture or intergrowth containing a chabazite and AEI framework with a molar relationship of:

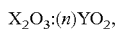
    $X_2O_3:(n)YO_2,$ wherein X is a trivalent element, Y is a tetravalent element and n is greater than 20; and
    forming the olefin product; and
    wherein the change from the first to second oxygenate feed is immediate.

2. The process of claim 1, wherein the oxygenate feed is contacted with the olefin forming catalyst at an average reactor temperature in the range of from 200° C. to 1000° C.

3. The process of claim 1, wherein n is at least 30.

4. The process of claim 1, wherein n is at least 50.

5. The process of claim 1, wherein n is at least 100.

6. The process of claim 1, wherein X is selected from aluminum, boron, iron, indium, and/or gallium and Y is selected from silicon, tin, titanium and/or germanium.

7. The process of claim 1, wherein X is aluminum and Y includes silicon.

8. The process of claim 1, wherein the contacting of the oxygenate with the olefin forming catalyst forms an olefin product having an ethylene to propylene weight ratio increased by at least 5% relative to that when using 100 wt % methanol as feed at the same conversion conditions.

9. The process of claim 1, wherein the olefin forming catalyst is contacted with the oxygenate feed until the olefin forming catalyst is deposited with a coke deposit of 20% or more, based on percent of maximum coke content, and the coke deposited catalyst is then contacted with a second oxygenate feed containing at least 50 wt % methanol, based on total weight of the second oxygenate feed.

10. The process of claim 1, wherein olefin from the olefin product is contacted with a polyolefin forming catalyst to form a polyolefin.

11. The process of claim 1, wherein at least one of the following is satisfied:
    (i) the olefin forming catalyst comprises at least in part a CHA type framework;
    (ii) the olefin product has an ethylene to propylene weight ratio of at least 1.0, when subject to an average reactor temperature from 200° C. to less than 520° C.; and
    (iii) the olefin product has an ethylene to propylene weight ratio of at least 1.35, when subject to an average reactor temperature from 520° C. to 1000° C.

12. A multi-staged process alternating contacting a catalyst with dimethyl ether (DME) and methanol for producing an olefin product, comprising:
    providing an olefin forming aluminosilicate catalyst comprising a porous crystalline aluminosilicate having a mixture or intergrowth containing a chabazite and AEI framework with a molar relationship of:

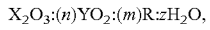
    $X_2O_3:(n)YO_2:(m)R:zH_2O,$ wherein X is a trivalent element, Y is a tetravalent element, n is greater than 20, R is a directing agent, m ranges from 15 to 350, and z ranges from 0 to 10;
    removing the directing agent to form an active olefin forming catalyst; and
    contacting in a first stage a first oxygenate feed consisting of less than 50 wt % dimethyl ether (DME) as well as diluent, based on the total weight of the feed, with the catalyst;
    contacting the active olefin forming catalyst in a second stage a second oxygenate feed consisting of at least 50 wt % methanol (MeOH) as well as diluent, based on total weight of the feed, to form the olefin product;
wherein the change from the first to second oxygenate feed is immediate.

13. The process of claim 12, wherein R comprises at least one cyclic amine or ammonium compound.

14. The process of claim 12, wherein R comprises at least one multi-cyclic amine or ammonium compound.

15. The process of claim 12, wherein m ranges from about 30 to about 50.

16. The process of claim 12, wherein n is at least 30.

17. The process of claim 16, wherein n is at least 50.

18. The process of claim 17, wherein n is at least 100.

19. The process of claim 12, wherein X is selected from aluminum, boron, iron, indium, and/or gallium and Y is selected from silicon, tin, titanium and/or germanium.

20. The process of claim 12, wherein X is aluminum and Y includes silicon.

21. The process of claim 12, wherein oxygenate feed contains at least 25 wt % dimethyl ether, based on total weight of the feed.

22. The process of claim 12, wherein the oxygenate feed is contacted with the olefin forming catalyst at an average reactor temperature in the range of from 200° C. to 1000° C.

23. The process of claim 12, wherein the contacting of the oxygenate with the olefin forming catalyst forms an olefin product having an ethylene to propylene weight ratio increased by at least 5% relative to that when using 100 wt % methanol as feed at the same conversion conditions.

24. The process of claim 12, wherein the olefin forming catalyst is contacted with the oxygenate feed until the olefin forming catalyst is deposited with a coke deposit of 20% or more, based on percent of maximum coke content, and the coke deposited catalyst is then contacted with a second oxygenate feed containing at least 50 wt % methanol, based on total weight of the second oxygenate feed.

25. The process of claim 12, wherein olefin from the olefin product is contacted with a polyolefin forming catalyst to form a polyolefin.

26. The process of claim 12, wherein at least one of the following is satisfied:
   (i) the olefin forming catalyst comprises at least in part a CHA type framework;
   (ii) the olefin product has an ethylene to propylene weight ratio of at least 1.0, when subject to an average reactor temperature from 200° C. to less than 520° C.; and
   (iii) the olefin product has an ethylene to propylene weight ratio of at least 1.35, when subject to an average reactor temperature from 520° C. to 1000° C.

* * * * *